United States Patent
Schoenbach et al.

(10) Patent No.: US 8,948,878 B2
(45) Date of Patent: Feb. 3, 2015

(54) METHOD AND DEVICE FOR TREATMENT OF CONDITIONS AGGRAVATED BY AMYLOID FIBRILS

(75) Inventors: Karl H. Schoenbach, Norfolk, VA (US); Lesley Greene, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 675 days.

(21) Appl. No.: 13/161,362

(22) Filed: Jun. 15, 2011

(65) Prior Publication Data

US 2011/0306962 A1 Dec. 15, 2011

Related U.S. Application Data

(60) Provisional application No. 61/355,013, filed on Jun. 15, 2010.

(51) Int. Cl.
*A61N 1/00* (2006.01)
*A61N 1/20* (2006.01)
(Continued)

(52) U.S. Cl.
CPC ............... *A61B 18/12* (2013.01); *A61N 1/205* (2013.01); *A61N 1/327* (2013.01); *A61B 18/1492* (2013.01); *A61B 2018/00446* (2013.01)
USPC ............. 607/72; 607/74; 607/76; 607/156; 128/898

(58) Field of Classification Search
USPC ............... 607/2, 72, 74, 76, 115, 154, 156; 435/171.1; 128/898
See application file for complete search history.

(56) References Cited

U.S. PATENT DOCUMENTS

| 8,688,227 B2 | 4/2014 | Nuccitelli et al. |
| 2003/0054990 A1 | 3/2003 | Averback |

(Continued)

FOREIGN PATENT DOCUMENTS

| EP | 1532976 A2 | 5/2005 | |
| WO | WO 2009013630 A2 * | 1/2009 | ............ A61K 41/00 |

(Continued)

OTHER PUBLICATIONS

Internation Search Report and the Written Opinion of the International Searching Authority; Issued Feb. 17, 2012; PCT/US2011/040572.

(Continued)

*Primary Examiner* — Linda Dvorak
*Assistant Examiner* — Adam Avigan
(74) *Attorney, Agent, or Firm* — Novak Druce Connolly Bove + Quigg LLP (57) ABSTRACT

A method and device for treating a condition aggravated by the presence of amyloid fibrils is disclosed. The method includes applying a plurality of ultra-short pulses to target tissue comprising amyloid fibrils. The plurality of ultra-short pulses produce an electric field in the target tissue sufficient to change a molecular structure of the amyloid fibrils without causing the death, destruction, or serious injury of healthy cells surrounding the target tissue. For example, the plurality of ultra-short pulses can be sufficient to change the molecular structure of amyloid fibrils without causing apoptosis or necrosis of surrounding cells. The ultra-short pulses can be applied using an electrode device or a wideband antenna. The ultra-short pulses can have a duration ranging from 1 ps to 10 ns, an amplitude ranging from 100 V to 1 MV, and can apply an electrical field to the target tissue ranging from 1 kV/cm to 1 MV/cm.

13 Claims, 8 Drawing Sheets

(51) Int. Cl.
*A61N 1/32* (2006.01)
*A61B 18/12* (2006.01)
*A61B 18/14* (2006.01)
*A61B 18/00* (2006.01)

(56) References Cited

U.S. PATENT DOCUMENTS

| | | |
|---|---|---|
| 2005/0214380 A1 | 9/2005 | Bruch et al. |
| 2007/0198068 A1 | 8/2007 | Chan et al. |
| 2008/0004364 A1* | 1/2008 | Huo et al. ............ 522/2 |
| 2009/0125091 A1* | 5/2009 | Schoenbach et al. ......... 607/156 |
| 2009/0299417 A1 | 12/2009 | Schoenbach et al. |
| 2010/0280513 A1 | 11/2010 | Juergen et al. |

FOREIGN PATENT DOCUMENTS

| | | |
|---|---|---|
| WO | 2009-046275 | 4/2009 |
| WO | WO 2010105035 A2 * | 9/2010 |
| WO | 2010120866 | 10/2010 |
| WO | 2010151370 | 12/2010 |

OTHER PUBLICATIONS

Camp et al., "Development of a high voltage, 150 ps pulse generator for biological applications", Proceedings of the Power modulator Conference Las Vegas, NV (2008): 338.

Chen et al., "Measurement of amyloid mass-per-length by tilted beam transmission electron microscopy", PNAS (2006) 106: 14339-14344.

Chiti et al., "Protein misfolding, functional amyloid and human disease", Ann Rev Biochem (2006) 75: 333-366.

Conway et al., "Accelerated in vitro fibril formation by a mutant alpha-synuclein linked early-onset Parkinson's Disease", Nature Medicine (1998) 4: 1318-1320.

De Ferrari et al., "Thioflavin T is a fluorescent probe of the acetylcholinesterase peripheral site that reveals conformational interactions between the peripheral and acylation sites", J Biol Chem (2000) 276: 23282-23287.

Eakin et al., "From chance to frequent encounters: Origina of beta2-microglobulin fibrillogenesis", Bichimica Biphysica Acta (2005) 1753: 92-99.

Hoyer et al., "Dependency of alpha-synuclein aggregate morphology on solution conditions", J Mol Biol (2001) 322: 383-393.

Irvine et al., "Protein aggregation in the brain: The molecular basis for Alzheimer's and Parkinson's disease", Mol Med (2008) 14: 451-464.

Momany et al., "Energy parameters in polypeptides. VII. Geometric parameters, partial atomic charges, nonbonded interactions, hydrogen bond interactions, and intrinsic torsional potentials for the naturally occurring amino acids", J Phys Chem (1975) 79: 2361-2381.

Nelson et al., "Structure of the cross-beta spine of amyloid-like fibrils", Nature (2005) 435: 773778.

Schoenbach et al., "The effect of intense subnanosecond electrical pulses on biological cells", IEEE Transaction on Plasma Science (2008) 36(2): 414-424.

Thompson, "Unraveling the secrets of Alzheimer's beta-amyloid fibrils", PNAS (2003) 100(2): 383-385.

* cited by examiner

METHOD AND DEVICE FOR TREATMENT OF CONDITIONS AGGRAVATED BY AMYLOID FIBRILS

TECHNICAL FIELD OF THE INVENTION

The invention relates to a method and device for treating conditions aggravated by amyloid fibrils, and more specifically to neurodegenerative diseases.

BACKGROUND OF THE INVENTION

Proteins contain polypeptide sequences that encode the protein's functional, stable, native three-dimensional state. In certain circumstances proteins misfold or are cut into peptides which then aggregate into a structure called amyloid fibrils. Regardless of the underlying protein or peptide, amyloid fibrils have a characteristic structure composed predominantly of beta-sheets which associate into an elongated fibular form. Amyloid fibrils are associated with a large number of neurodegenerative diseases, which include, but are not limited to, Alzheimer's and Parkinson's disease. See: Chin, F. and Dobson, C M. (2006) Protein misfolding, functional amyloid and human disease. *Ann. Rev. Biochem,* 75, 333-366. There are also other debilitating diseases where amyloid fibrils form deposits in areas outside of the central nervous system. These include intra-articular spaces as in the case of prolonged-renal dialysis associated amyloidosis. See: Eakin, C. M. and Miranker, A. D., "From chance to frequent encounters: origins of β2-microglobulin fibrillogenesis," *Biochimica Biphysica Acta* 1753, 92-99 (2005). Diseases that are linked to the presence of amyloid fibrils include, but are not limited to: type 2 diabetes mellitus, transmissible spongiform encephalopathy (e.g., Bovine Spongiform Encephalopathy aka "Mad Cow Disease"), Huntington's disease, medullary carcinoma of the thyroid, cardiac arrhythmias, atherosclerosis, rheumatoid arthritis, aortic medial amyloid, prolactinomas, familial amyloid polyneuropathy, hereditary non-neuropathic systemic amyloidosis, dialysis related amyloidosis, Finnish amyloidosis, lattice corneal dystrophy, cerebral amyloid angiopathy, cerebral amyloid angiopathy (Icelandic type), systemic AL amyloidosis, yeast prions, sporadic inclusion body myositis, pheochromocytoma, osteomyelitis and multiple myeloma. At present there is no cure for amyloid-related diseases. Thus, techniques for treating amyloid-related diseases in the body are needed.

SUMMARY OF THE INVENTION

A device and method for the treatment of neurodegenerative diseases is disclosed.

A first embodiment relates to a method for treating a condition aggravated by the presence of amyloid fibrils. The method can comprise applying one or more ultra-short pulses to target tissue comprising amyloid fibrils, wherein each ultra-short pulse produces an electrical field in the target tissue, and wherein the one or more ultra-short pulses are sufficient to change a molecular structure of said amyloid fibrils without causing the death, destruction, or serious injury of healthy cells surrounding the target tissue. For example, the one or more ultra-short pulses can be sufficient to change the molecular structure of amyloid fibrils without causing apoptosis or necrosis of healthy cells surrounding said target tissue. A duration of at least one of said one or more ultra-short pulses can range from 1 ps to 1 ms. An electrical field applied to said target tissue by said one or more ultra-short pulses can range from 1 kV/cm to 1 MV/cm. An amplitude of at least one of the one or more ultra-short pulses can range from 100 V to 1 MV. The target tissue can comprise brain tissue, pancreas tissue, heart tissue, or intra-articular tissue. The change in molecular structure can comprise breaking hydrogen bonds.

The method can further comprise positioning an electrode device comprising a working electrode within a subject being treated such that each ultra-short pulse produces an electrical field in said target tissue ranging from 1 kV/cm to 1 MV/cm. The electrode device can comprise a wave guide, positioned within a catheter.

The method can further comprise positioning an antennae transmitting electromagnetic radiation as a result of receiving said one or more ultra-short pulses thereby producing an electrical field in said target tissue ranging from 1 kV/cm to 1 MV/cm. The antennae can be external to a subject being treated.

The method can further comprise diagnosing the target tissue comprising amyloid fibrils to which the one or more ultra-short pulses will be applied.

A second embodiment relates to a system for changing the molecular structure of amyloid fibrils. The system can comprise a power source for generating a one or more ultra-short pulses; and a delivery system in communication with said power source for applying said one or more ultra-short pulses to target tissue comprising amyloid fibrils, wherein each ultra-short pulse produces an electrical field in the target tissue, and wherein the one or more ultra-short pulses are sufficient to change a molecular structure of said amyloid fibrils without causing the death, destruction, or serious injury of healthy cells surrounding the target tissue. For example, the one or more ultra-short pulses can be sufficient to change the molecular structure of amyloid fibrils without causing apoptosis or necrosis in healthy cells surrounding said target tissue.

The delivery system can comprise one or more electrode devices. At least one of the one or more electrode devices can be positioned within a catheter.

The at least one of the one or more ultra-short pulses can have duration between 1 ps and 1 ms. The amplitude of at least one of the one or more ultra-short pulses can range from 100 V to 1 MV. The one or more ultra-short pulses can have a rise time ranging from 0.5 picoseconds to 1 nanosecond.

The delivery system transmitting the one or more ultra-short pulses can produce an electric field at the target ranging from 1 kV/cm to 11\TV/cm. The ultra-short pulses can be monopolar, bipolar, or oscillating.

The delivery system can comprise a wideband antenna. A focusing element of said wideband antenna can comprise at least one of a prolate spheroidal reflector and a lens. Wideband radiation generated by the antenna can generate electric fields in the target tissue ranging from 1 kV/cm to 1 MV/cm.

BRIEF DESCRIPTION OF THE DRAWINGS

A fuller understanding of the present invention and the features and benefits thereof will be obtained upon review of the following detailed description together with the accompanying drawings, in which:

FIGS. 6A and B are control TEM images of fibrils formed with α-synuclein;

FIGS. 6C-F are TEM images of fibrils formed with α-synuclein and subjected to varying pulses;

For a better understanding of the present invention, together with other and further objects, advantages and capabilities thereof, reference is made to the following disclosure and appended claims in connection with the above-described drawings.

DETAILED DESCRIPTION OF THE INVENTION

Applicants have discovered that it is possible to apply electric fields in ultra-short pulses to break up amyloid Amyloid fibrils were previously thought to be homogenous in structure, but applicants have unexpectedly discovered that amyloid fibrils have weak points within their structure that break more easily than other points. Once the amyloid fibrils are broken, the body can eliminate them. The smaller the fibril fragments, the easier for the body to dispose of. The concept of "weak points" can be used to fine tune the parameters of the method, i.e., provide only pulses having a duration and/or field strength sufficient to break the weak points. The technique of applying electric fields in ultra-short pulses to break up amyloid fibrils is of particular interest, because much higher electrical fields than those used to breakdown the amyloid fibrils are required to cause cell death. Thus, the process is capable of breaking down the amyloid fibrils with the unexpected benefit that the method does not cause death, destruction, or serious injury of healthy cells surrounding the amyloid fibrils.

Because the method is based on breaking weak bonds in proteins, it can also be applied to proteins other than amyloid fibrils, opening up other therapeutic applications besides treatment of neurodegenerative diseases. As discussed above, diseases that are linked to the presence of amyloid fibrils include, but are not limited to: type 2 diabetes mellitus, transmissible spongiform encephalopathy (e.g., Bovine Spongiform Encephalopathy aka "Mad Cow Disease"), Huntington's disease, medullary carcinoma of the thyroid, cardiac arrhythmias, atherosclerosis, rheumatoid arthritis, aortic medial amyloid, prolactinomas, familial amyloid polyneuropathy, hereditary non-neuropathic systemic amyloidosis, dialysis related amyloidosis, Finnish amyloidosis, lattice corneal dystrophy, cerebral amyloid angiopathy, cerebral amyloid angiopathy (Icelandic type), systemic AL amyloidosis, yeast prions, sporadic inclusion body myositis, pheochromocytoma, osteomyelitis and multiple myeloma. Applying electric fields in ultra-short pukes to break up amyloid fibrils can be used to treat these and other diseases caused or aggravated by amyloid fibrils, including neurodegenerative diseases, such as Parkinson's and Alzheimer's diseases.

In several embodiments, ultra-short pulses can be applied in a targeted manner to the parts of the body, such as the brain, which are affected. Before specific areas can be targeted, amyloid fibrils must be diagnosed, and precisely located. Therefore, some embodiments include one or more diagnostic steps. According to an exemplary diagnostic method, amyloid fibrils can first be identified. The term "identified" in this context means diagnosed and precisely located.

Any method for identifying, diagnosing, and/or locating amyloid fibrils can be employed. For example, the diagnostic method can include using dyes and/or chemically-labeled compounds with an affinity for amyloid fibrils to mark amyloid fibrils. The marked amyloid fibrils can then be detected using various medical imaging methods, such as CAT or PET scanning. An exemplary compound suitable for marking amyloid fibrils is Florbetapir F 18 (18 F-AV-45), which has shown preliminary affinity and specificity to beta-amyloid. Therefore, according to various embodiments, Florbetapir F 18 (18 F-AV-45), can be used with positron emission tomography (PET) technology to detect beta-amyloid plaque deposits in living patients. Other diagnostic methods include x-ray, and scintirgraphy techniques.

Next, the diagnostic method can include devising a treatment modality for the specific location identified as having amyloid fibrils. Devising a treatment modality can take into consideration a number of factors, including, but not limited to tissue type, fibril size, type, and number. The treatment modality can include, but is not limited to specifying a pulse width, a pulse frequency, a amplitude, a pulse duration, and/or an electric field strength. The treatment device is then positioned so as to deliver the pulses to the targeted location. The positioning can include locating a probe adjacent to the location, or directing an antenna such that the pulses are directed at the location.

The ultra-short pulses can be applied using a variety of devices, including catheter-type electrode devices, e.g., waveguides or cables, and focusing wideband antennas.

In one embodiment, the method is drawn to a method for treating a condition aggravated by, caused by, or otherwise related to the presence of amyloid fibrils. The method can include applying one or more ultra-short pulses to target tissue comprising amyloid fibrils. The one or more ultra-short pulses can produce electrical fields in the target tissue sufficient to change the molecular structure of the amyloid fibrils without causing the death, destruction, or serious injury of healthy cells surrounding the target tissue. For example, the one or more ultra-short pulses can be sufficient to change the molecular structure of amyloid fibrils without causing apoptosis or necrosis of healthy cells surrounding the amyloid fibrils and/or in the target tissue. The target tissue can be any type of tissue, including but not limited to brain tissue, intraarticular tissue, pancreas tissue, heart tissue, or any other tissue containing amyloid fibrils to be treated.

An amyloid fibril is a quaternary structure. Therefore, an amyloid fibril includes primary, secondary, and tertiary structures. A primary structure can be a sequence of amino acids. A secondary structure can include beta-sheets, alpha-helices and loops formed from primary structures. A tertiary structure can comprise an association or packing of secondary structures to form a globular protein. A quaternary structure can comprise an association of tertiary structures to form a higher order structure, such as an amyloid fibril.

As used herein, the term "change a molecular structure of the amyloid fibrils" encompasses any alteration to an amyloid fibril that produces an arrangement that is distinct from a mature fibril or proto-fibril. The change to the molecular structure of the amyloid can be reversible or irreversible, but irreversible changes are more apt to lead to effective removal and/or treatment of the fibrils. Without wishing to be bound by theory, the change to the molecular structure of the amyloid fibril can include a morphological change resulting from a chemical and/or structural change to the fibril. The change to the molecular structure can be a shift from a quaternary structure to a tertiary, secondary, and/or primary structure, or a change to any of the quaternary, tertiary, secondary, or primary structures. The change in the molecular structure of the amyloid fibrils can be sufficient to allow the amyloid fibrils to be naturally eliminated by the patient's body. The change in molecular structure can be the breaking of bonds between the proteins forming the amyloid fibrils. The bonds can be weak bonds such as hydrogen bonds. The bonds can also be ionic, covalent, and/or polar covalent bonds. Consequently, the application of a high electrical field can be sufficient to break-apart, fragment, or destroy the amyloid fibril.

A variety of techniques can be employed to determine the degree of change to a molecular structure of the amyloid fibrils by the ultra-short pulses. For example, samples of treated tissue can be tested with column chromatography, SDS-PAGE gel electrophoresis, mass spectroscopy, circular dichroism, western blots, transmission electron microscopy, atomic force microscopy, and/or cell culturing.

As used herein, the term "ultra-short pulse" describes a pulse with a duration ranging from 0.1 picoseconds (ps) to 1 microseconds (ms). The ultra-short pulses can have a duration within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, and 1000000 picoseconds. For example, the ultra-short pulses can have a duration ranging from 0.10 ps to 1 ms, or from 10 ps to 1 ns, or from 25 ps to 750 ps, or any combination thereof, e.g., 1 to 25 ps or 1 to 750 ps. The ultra-short pulses can be monopolar, bipolar or oscillating. The ultra-short pulses can have arise time within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, and 1000 picoseconds. For example, the ultra-short pulses can have a rise time ranging from 0.5 picoseconds to 1 nanosecond.

The electrical field applied to the target tissue by the plurality of ultra-short pulses can fall within a range having a lower limit and/or an upper limit. The range can include or exclude the lower limit and/or the upper limit. The lower limit and/or upper limit can be selected from 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, and 1000 kV/cm. For example, the electrical field applied to the target tissue by the plurality of ultra-short pulses can range from 1 kV/cm to 1 MV/cm. The electrical field applied to the target tissue can also range from 10 kV/cm to 700 kV/cm, or from 20 kV/cm to 500 kV/cm, or from 25 kV/cm to 400 kV/cm.

The combination of the duration and the amplitude of the ultra-short pulses does not mandate any particular frequency of ultra-short pulses. The frequency of the ultra-short pulses can depend on the operator of the apparatus used to apply the pulses in various experiments, a 10 Hertz frequency was used to apply 16,000 pulses to finish the experiment as quickly as possible. The goal is to create an electrical effect while avoiding a thermal effect. Applying pulses at an extremely high frequency could create a thermal effect. It was discovered that applying 32,000 pulses resulted in a 1 degree Celsius temperature increase. The ultra-short pulses can be applied at a frequency that falls within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, and 10,000 Hertz. For example, the ultra-short pulses can be applied at a frequency in a range of from 1 Hertz to 10 Kilohertz.

The method can also include positioning an electrode device comprising a working electrode within a subject being treated such that each ultra-short pulse produces an electrical field in the target tissue ranging from 1 kV/cm to 1 MV/cm. The electrode device can be attached at the end of a long-narrow medical instrument, such as a catheter or probe, so that the ultra-short pulses can be directed at internal tissue, such as the brain or intra-articular tissue. An electrode of the electrode device can be contacted with or inserted into the target tissue.

As used herein, an "electrode device" refers to any device with at least one electrode capable of delivering ultra-short pulses to target tissue and producing an electrical field within the target tissue. Electrode devices include, but are not limited to, waveguides, such as coaxial cables, single needle devices and multi-needle devices. These devices would be placed in catheters and inserted into the target tissue. Exemplary electrode devices useful for the methods and devices disclosed herein include those disclosed in U.S. patent application Ser. No. 12/599,259 filed Nov. 6, 2009; U.S. Pat. Ser. No. 12/418,864 filed Apr. 6, 2009; and PCT Application No. PCT/US2010/031014 filed Apr. 14, 2010; and U.S. application Ser. No. 12/759,853, the entireties of which are incorporated herein by reference.

The method can also include positioning an antennae transmitting electromagnetic radiation to produce an electrical field in the target tissue ranging from 1 kV/cm to 1 MV/cm. The electrical field can be produced when the ultra-short pulse reaches the antenna and electromagnetic radiation is generated by the antenna. Exemplary antennae and antennae systems useful for the methods and devices disclosed herein include, but are not limited to, those disclosed in PCT Application No. PCT/US2010/032979 filed Apr. 29, 2010, the entirety of which is incorporated herein by reference. The wideband antenna can include at least one of a prolate spheroidal reflector and a lens.

The antennae can be positioned external to a subject being treated. Alternately, a suitably configured antenna can be positioned within the subject being treated.

In another embodiment, a system for changing the molecular structure of amyloid fibrils is disclosed. The system can include a power source for generating a plurality of ultra-short pulses and a delivery system in communication with the power source for applying the plurality of ultra-short pulses to target tissue. The plurality of ultra-short pulses can cause changes in the molecular structure of the amyloid fibrils without causing the death, destruction, or serious injury of healthy cells surrounding the target tissue. For example, the plurality of ultra-short pulses can be sufficient to change the molecular structure of amyloid fibrils without causing apoptosis or necrosis in cells surrounding target tissue. The delivery system can include one or more electrode devices, one or more wideband antenna, or a combination of both. Thus, the invention is also drawn to use of the devices described herein for treating conditions aggravated by amyloid fibrils.

Examining amyloid fibrils by X-ray fiber diffraction indicates that the fibrils contain beta strands that are perpendicular to the fiber axis, with inter-strand hydrogen bonding parallel to the fiber axis, and suggests that six peptide ribbons interact via backbone hydrogen bonds. In order to break these hydrogen bonds by means of external electric fields, the applied electric field strength needs to exceed the intra-molecular electrostatic fields between the donor and acceptor pair in the hydrogen bond. An estimate of the required field strength can be made by considering dipole-dipole interaction described by:

$$V = A/r^9 - Cr^6 + Z_1 Z_2 e^2 / 4\pi\epsilon r$$

where V is the potential energy, A and C are coefficients of the repulsive and attractive terms of the van der Waals interaction, and $Z_1$ and $Z_2$ are the partial charges of the two atoms which form the hydrogen bond (e is the elementary charge), and r is the distance between the charges.

Each GNNQQNY molecule forms 11 hydrogen bonds to its two neighboring molecules in the same beta-sheet. Five of them are backbone C=O.H—N hydrogen bonds and 4 are amide-amide hydrogen bonds between pairs of identical Asn or Gln residues in adjacent molecules within a beta-sheet.

Assuming van der Waals interactions don't play a role is not appropriate in vivo, but breaking hydrogen bonds preferentially will play a pivotal role in disrupting fibril structure even with van der Waals interactions involved. Therefore, assuming that the van der Waals interactions don't play a significant role. V can be calculated. For a Gln hydrogen bond, $Z_1(H^\beta)$ is 0.02 and $Z_2(O^{\delta 1})$ is −0.38. The distance between the charges is 0.32 nm for Gln5. The effect of the neighboring charges is assumed to be contained in a relative dielectric constant. For proteins a typical value is 3.5.

$$V = Z_1 Z_2 e^2 / 4\pi\epsilon r$$

V is in this case 9.8 meV, which corresponds to 0.22 kcal/Mole. In order to break this bond, electric fields greater than:

$$E = V/Z_1 e r$$

are required. This is the electric field generated by the smaller charge at the position of the larger charge. The calculated critical field intensity, E, is in this case 80 MV/in or 800 kV/cm.

These are tremendous electric fields. However, if the protein is immersed in a solution with a higher dielectric constant, e.g., water with a relative dielectric constant of 81, the potential energy becomes lower by a factor of $\epsilon_{water}/\epsilon_{protein} = 23$. That means that the potential energy, V, is approximately 0.43 meV, and the electric field intensity required for breaking the bond is 34.7 kV/cm. Since the potential energy of the hydrogen bond is not a static value, but fluctuates in time due to temperature motion, for very short times determined by oscillations of the dipole, the potential energy and the electric field intensity required for breaking the hydrogen bond might be even lower.

Figure 1A:
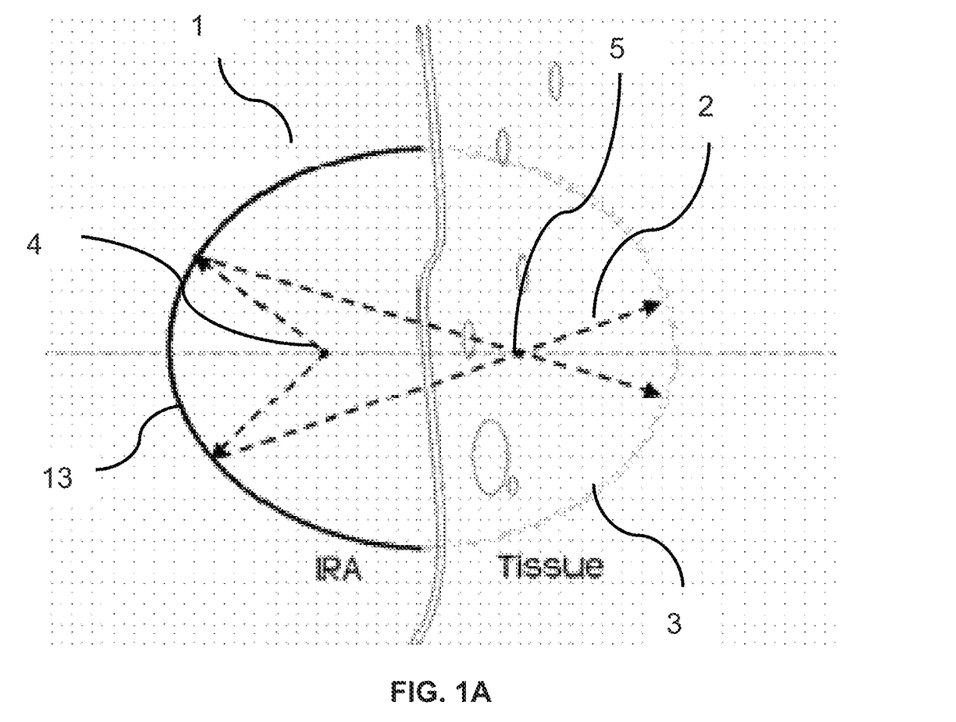
FIG. 1A is a schematic diagram of electromagnetic waves emitted from one focal point of a prolate-spheroid antenna focused in a second focal point inside a body.
Figure 1B:
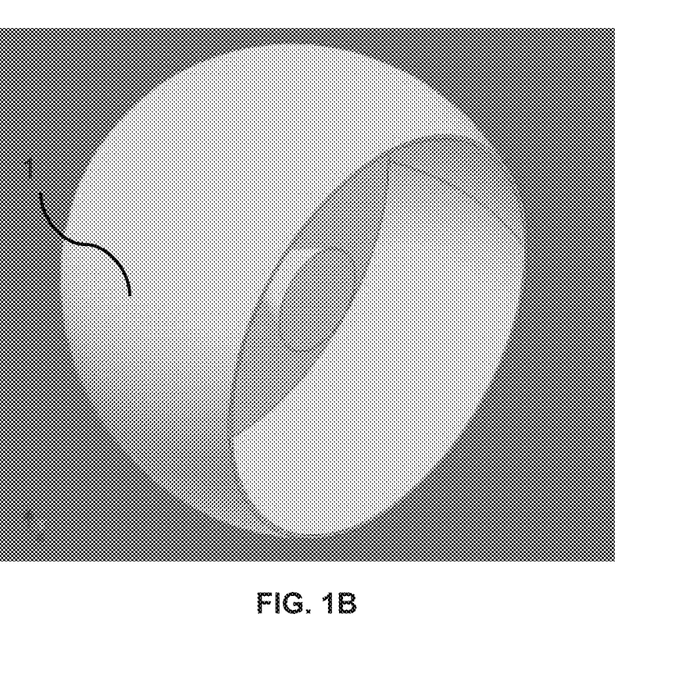
FIG. 1B, is a schematic diagram of a prolate-spheroid antenna.

According to one embodiment, applying ultrashort pulse effects for the interruption of fibrils involves the use of wide band antennas for the delivery of extremely high electric fields in vivo. Based on the current state of the art, electric field intensities of up to 100 kV/cm in tissue are readily achievable. However, higher electric field intensities can be provided. The maximum field intensity is a function of the ultra-short pulses; shorter pulses require a more intense electric field and longer pulses require a less intense electrical field to achieve similar effects. This definitely covers the range of calculated electric fields, assuming that the dielectric constant of the medium where they are embedded is close to that of water, e.g., bodily fluids, such as blood or plasma. FIG. 1A is a schematic diagram of electromagnetic waves 2 emitted from one focal point 4 of a prolate-spheroid antenna 1, having a reflector 13, focused in a second focal point 5 inside tissue 3 of a body. FIG. 1B is a schematic diagram of the prolate-spheroid antenna 1. Instead of using just a reflector 13 as shown in FIG. 1A, it is also possible to utilize a lens, either by itself or in conjunction with the reflector.

Figure 2:
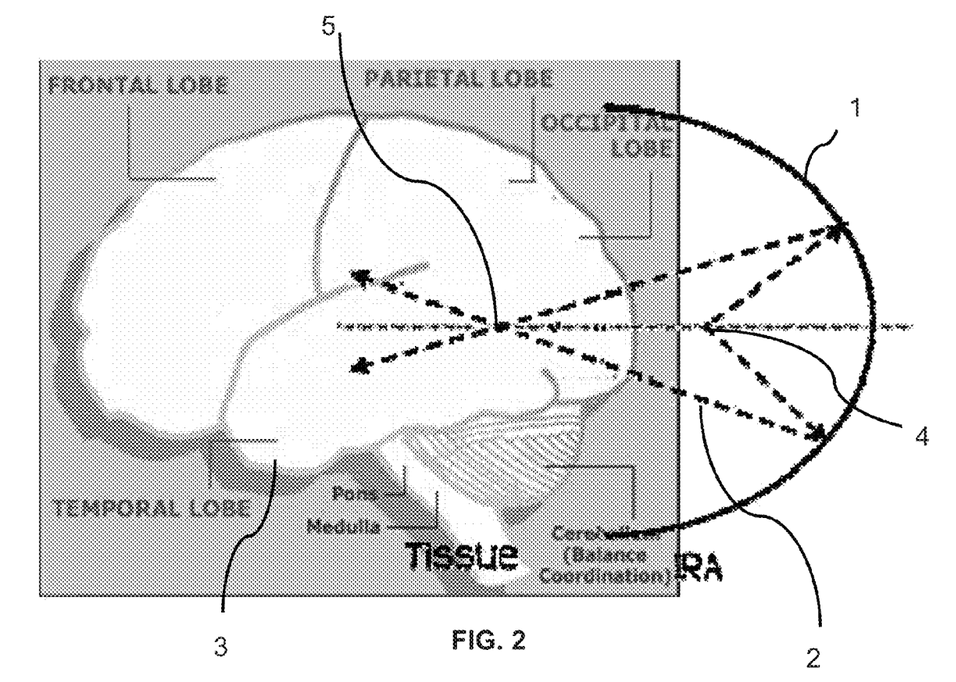
FIG. 2 is a schematic of a focusing antenna used to treat brain tissue.
Figure 3:
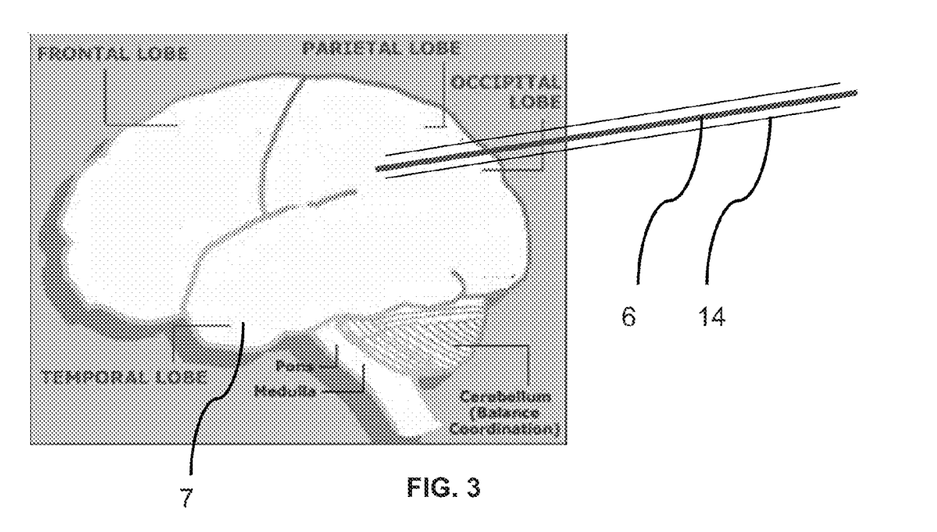
FIG. 3, is a schematic of a coaxial cable (waveguide) inserted into a brain.

Such an antenna 1 can be placed close to the region of the target tissue 3, e.g., the brain, which is affected (plaque) and by using ultrashort pulses the electromagnetic radiation can be focused onto the region of the brain where the structure of fibrils is affected. A figure showing such a configuration is illustrated in FIG. 2. More specifically, FIG. 2 is a schematic of a focusing antenna 1 used to treat tissue 3. As illustrated in FIG. 3, the tissue 3 is brain tissue, however, any type of tissue can be targeted. The focusing antenna 1 emits electromagnetic waves 2 from focal point 4. The waves 2 are focused in a second focal point 5 inside the tissue 3.

Instead of using a focusing antenna 1, such as that shown in FIG. 2, it is also possible to use waveguides, e.g., coaxial cables, to transfer ultrashort pulses to the tissue to be treated using a catheter-type pulse delivery devices. FIG. 3 is a schematic of a coaxial cable (waveguide) 6, positioned within a catheter 14 and inserted into tissue 7. As illustrated in FIG. 3, the tissue 7 is brain tissue, however the catheter-type pulse delivery devices can be employed in any type of tissue. By applying an ultra short pulse at A, an electric field is generated at the tip of the coaxial cable. Since these methods are based on breaking weak bonds in proteins, they can also be applied to disrupt proteins other than fibrils.

Other illnesses which may possibly be treated by this methodology include arthritic diseases, gout, cataracts, blood clots, kidney and gall bladder stones, scleroderma and arteriole diseases such as hardening of the arteries. Here, whether the target matter is calcium deposits, uric acid crystals or protein aggregation, the problematic structures can be harmlessly broken down by the electrical fields and thus relieve suffering. Thus the range of applications may be more broadly applicable than proposed for fibril-related diseases.

The function and advantage of these and other embodiments of the present invention will be more fully understood from the examples described below. The following examples are intended to facilitate an understanding of the invention and to illustrate the benefits of the present invention, but are not intended to limit the scope of the invention.

Examples

Figure 4A:
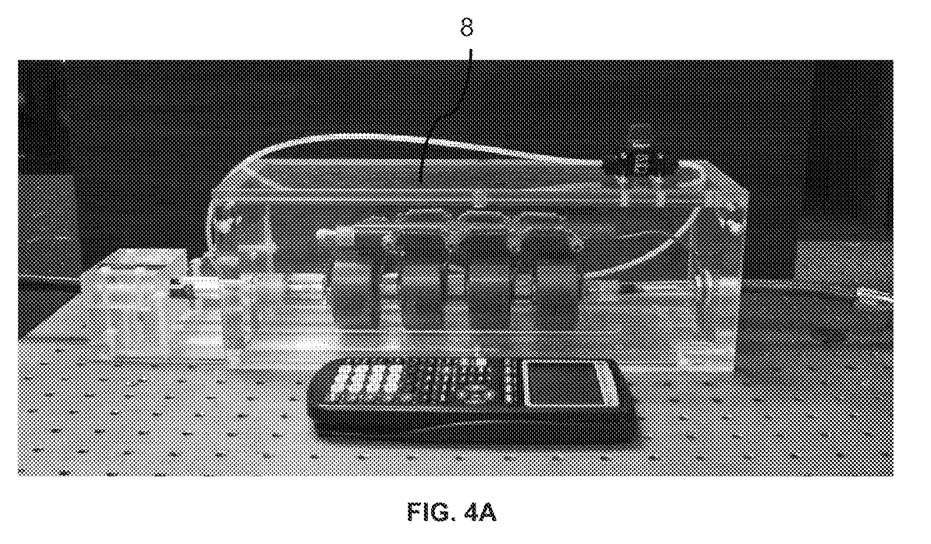
FIG. 4A is a photograph of a 150 ps, 20 kV pulse power generator.
Figure 4B:
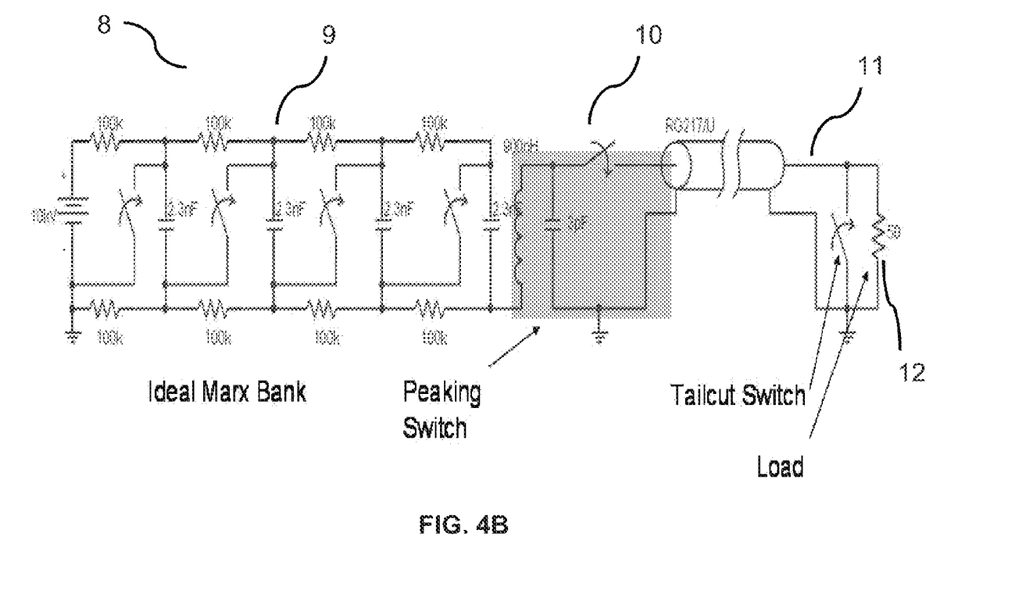
FIG. 4B is a schematic diagram of the electric circuit of the device.
Figure 5A:
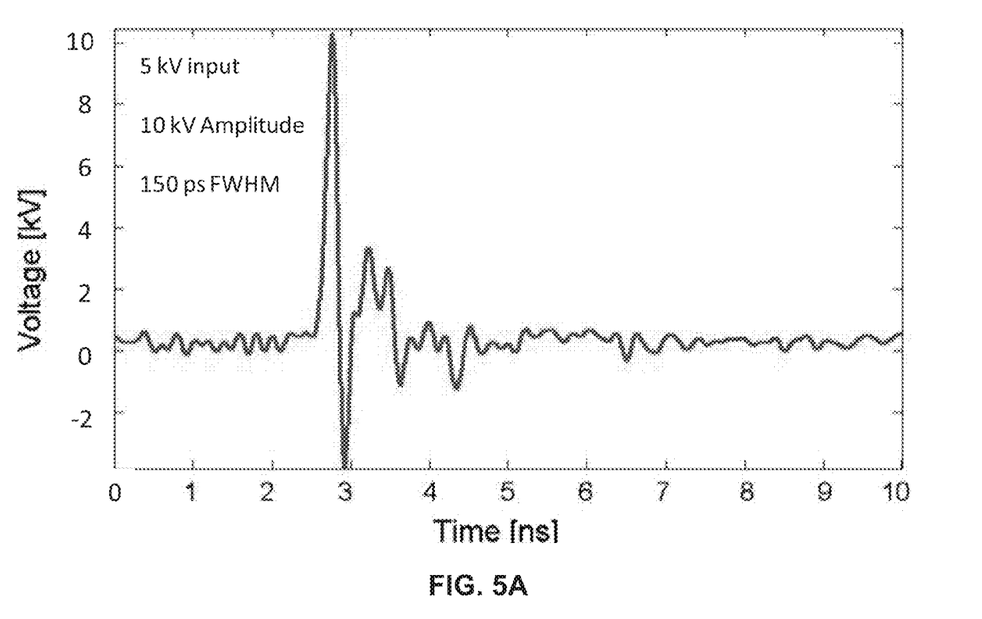
FIG. 5A is a graph of a pulse shape of a 150 ps pulse with an amplitude of 5 kV.
Figure 5B:
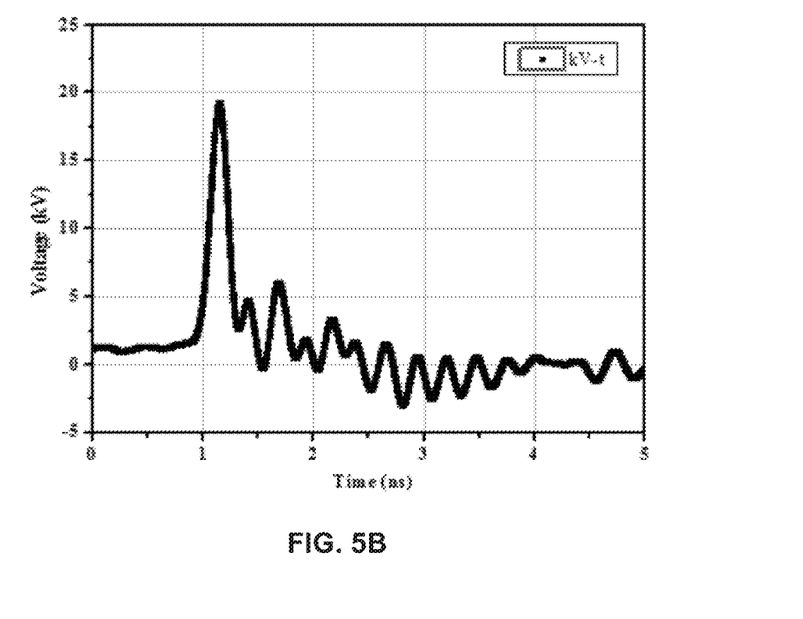
FIG. 5B is a graph of a pulse shape of a 200 ps long pulse with an amplitude of 18 kV.

Experimental studies have confirmed the theoretical considerations. A pulsed power device with pulse durations of 150 to 200 ps and amplitude of 20 kV was used in these experiments. The core of a pulse generator is the pulse-forming network. A photograph of a 150 ps pulse generator is shown in FIG. 4A together with the circuit diagram shown in FIG. 4B. FIG. 4A is a photograph of a 150 ps, 20 kV pulse power generator 8. A circuit diagram of the pulse generator, including the pulse-forming network, and the two switches (peaking switch and tailcut switch) which are used to generate to shape the high-voltage pulse are shown in FIG. 4B. The device 8 can comprise an Ideal Marx Bank 9, a Peaking Switch 10, a Tailcut Switch 11, and a load 12. The pulse, which has been recorded with a 4 GHz oscilloscope, is shown in FIG. 5A. More specifically, FIG. 5A shows the pulse shape of 150 ps pulse with amplitude of 5 kV. The Pulse shape of a 200 ps long (FWHM) pulse with an amplitude of 18 kV is shown in FIG. 5B.

Higher voltages and consequently higher pulsed electric fields on the order of 1 MV/cm in solutions containing cells can be obtained in vitro by using advanced pulsed power technology. The pulse duration can be 700 ps. Generally, the shorter the pulses the higher the threshold is for electrical breakdown. The calculated electric fields are consequently in the range where pulsed power technology is available. In addition, because of the extremely short duration of the pulses, the effects on cells, or in this case, fibrils, are purely electrical. The energy carried by these pulses is so low that, for single shot experiments, the increase in temperature is much less than one degree Celsius. Thus, any observed effect is clearly a nonthermal effect.

A model protein (human α-synuclein) was selected to develop the methodology of using high-intensity, ultra-short pulses to disrupt amyloid fibril structure. This model protein is associated with Parkinson's disease. Using the Lansbury method, human wild type α-synuclein was expressed in *Escherichia coli BL*21 DE3 cells using the recombinant pT7-7/human α-synuclein WT plasmid. Following induction with 1 mM isopropyl-β-D-thiogalactoside, bacterial cells were harvested by centrifuging at 5000 rpm at 4° C. for 30 minutes. Cells were lysed in 20 ml solution of 20 mM Tris Base, 1 mM ethylenediaminetetraacetic acid, 1 mM phenyl methane sulfonyl fluoride and further split open by sonication.

The lysate was boiled in a hot water bath at 100° C. for 30 minutes and then centrifuged at 10,000 rpm at 4° C. for 90 minutes. Streptomycin cut at 10 mg/ml was made to precipitate nucleic acids from the supernatant. An ammonium sulfate cut was made at 361 mg/ml to precipitate α-synuclein protein from supernatant. An α-synuclein pellet was dissolved in 20 mM Tris Base solution at pH 8.5 and loaded onto a Q-Sephadex anion exchange column and eluted with a 1 M NaCl gradient. The α-synuclein containing fraction was dialyzed against distilled deionized water for three days. A G-75 Sephadex gel chromatography column was used for further protein purification. Purified α-synuclein samples were lyophilized and stored at −80° C. Known techniques were used to form α-synuclein fibrils. Protein as a concentration of 4-6 mg/ml was dissolved in a buffer solution of 0.2M NaCl in 20 mM Tris Base, pH 7.5 and incubated at 37° C. an incubator shaking at 150-190 rpm. Fibril formation was monitored by Thioflavin T fluorescence. After all protein was converted to amyloid five 10 µl aliquots of fibril solution were adsorbed to the carbon films of Formvar carbon supports on 400 mesh copper grids. After 60 seconds of adsorption, solution was blotted and grid washed several times with distilled deionized water (5 µl, 7 seconds each), then blotted and dried in air.

α-Synuclein fibrils on the grid were stained with 10 µl of 2% uranyl acetate for 25 seconds before final blotting, washing and drying. Grids were examined for α-synuclein under an electron microscope.

Figure 6:
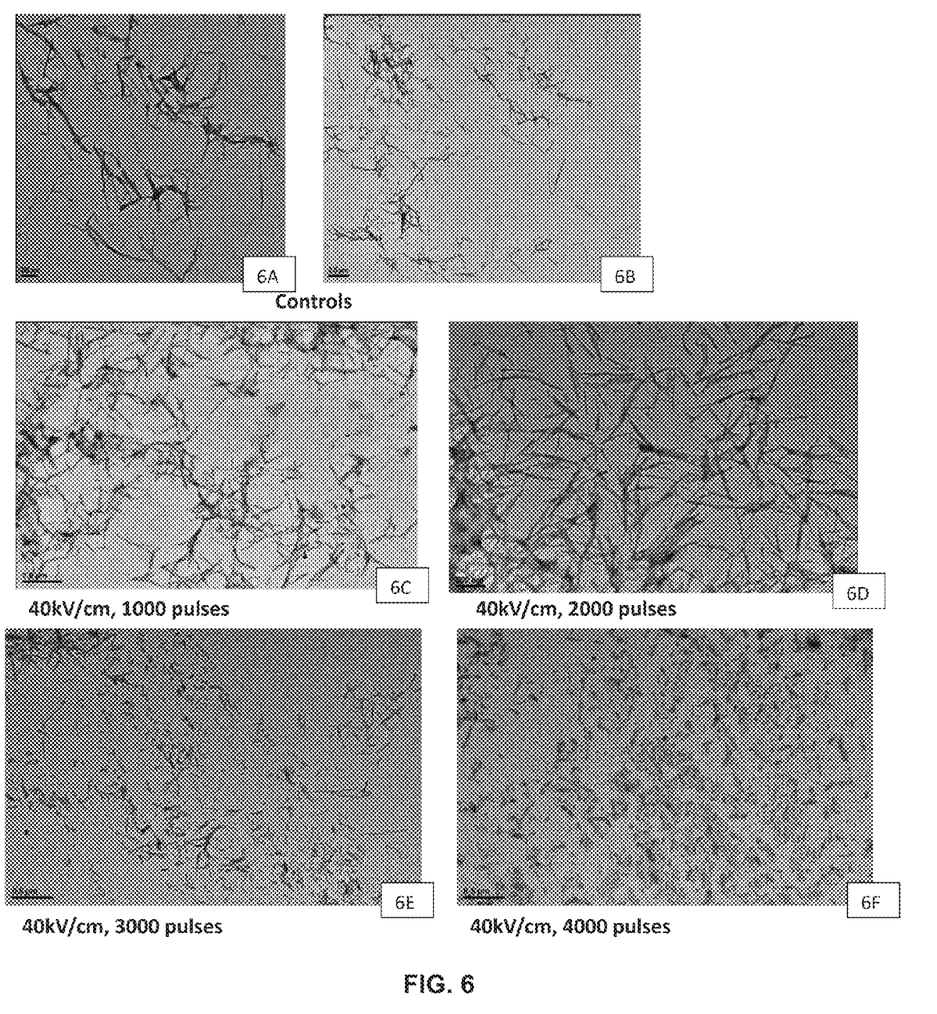
Figure 7:
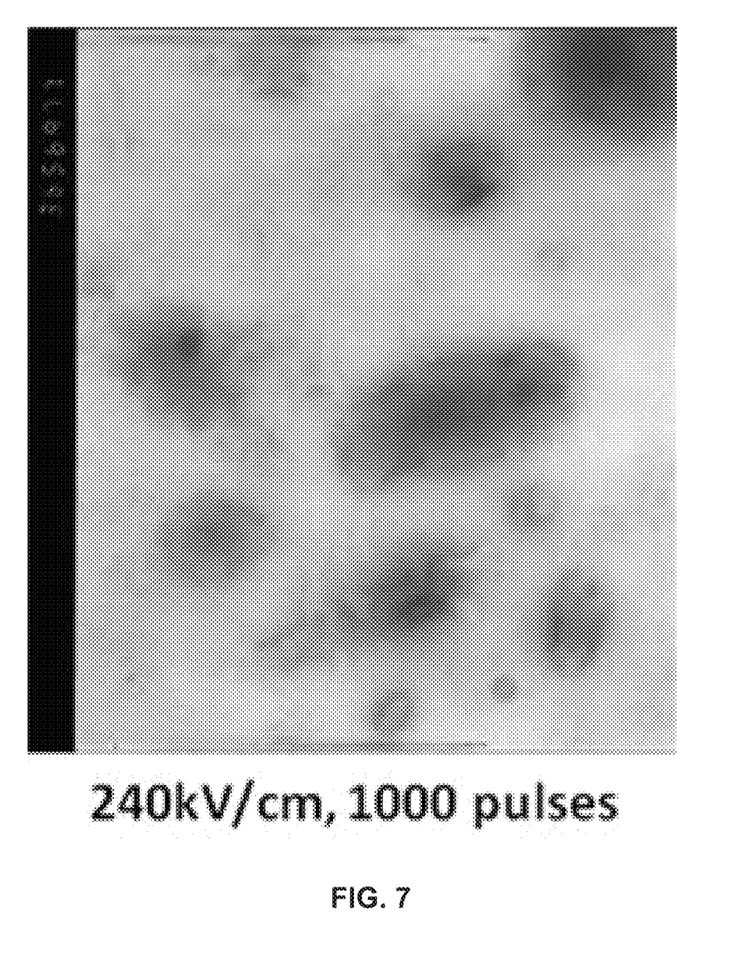
FIG. 7 is an image depicting a rearrangement of fibrils into spherical structures when exposed to high electric field pulses.

Amyloid fibrils can be visualized using Transmission Electron Microscopy (TEM). FIG. 6 shows the results of the above studies using TEM imaging. FIGS. 6A and B are control TEM images of fibrils formed with α-synuclein. FIGS. 6C-F are TEM images of fibrils formed with α-synuclein and subjected to varying pulses. The control TEM image shows elongated fibrils at varying stages of maturity. After the pulse is applied, distinctive changes in fibril morphology (breakage of the fibrils) are observed after both 3000 and 4000 pulses producing an electric field of 40 kV/cm. Interestingly after 1000 pulses producing a 240 kV/cm electric field, complete disruption of the fibrils is clearly evident and it appears as if the fibrils are forming very large spherical structures as shown in FIG. 7. More specifically, FIG. 7 is an image depicting a rearrangement of fibrils into spherical structures when exposed to high electric field pulses.

Figure 8:
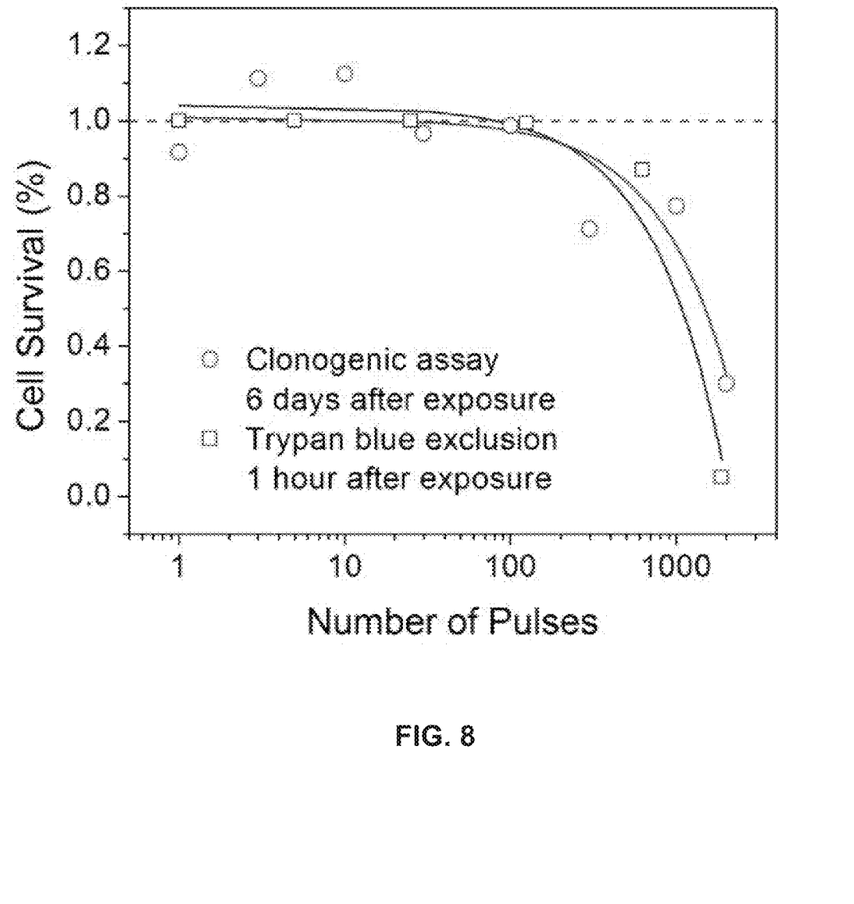
FIG. 8 is a graph depicting Trypan blue exclusion, 1 hour after pulsing, and caspase activity, measured 4.5 hours after pulsing, versus number of 800 ps pulses with average electric field amplitudes of 550 kV/cm (trypan blue exclusion) and 49-kV/cm. (caspase activity), respectively.
Figure 9:
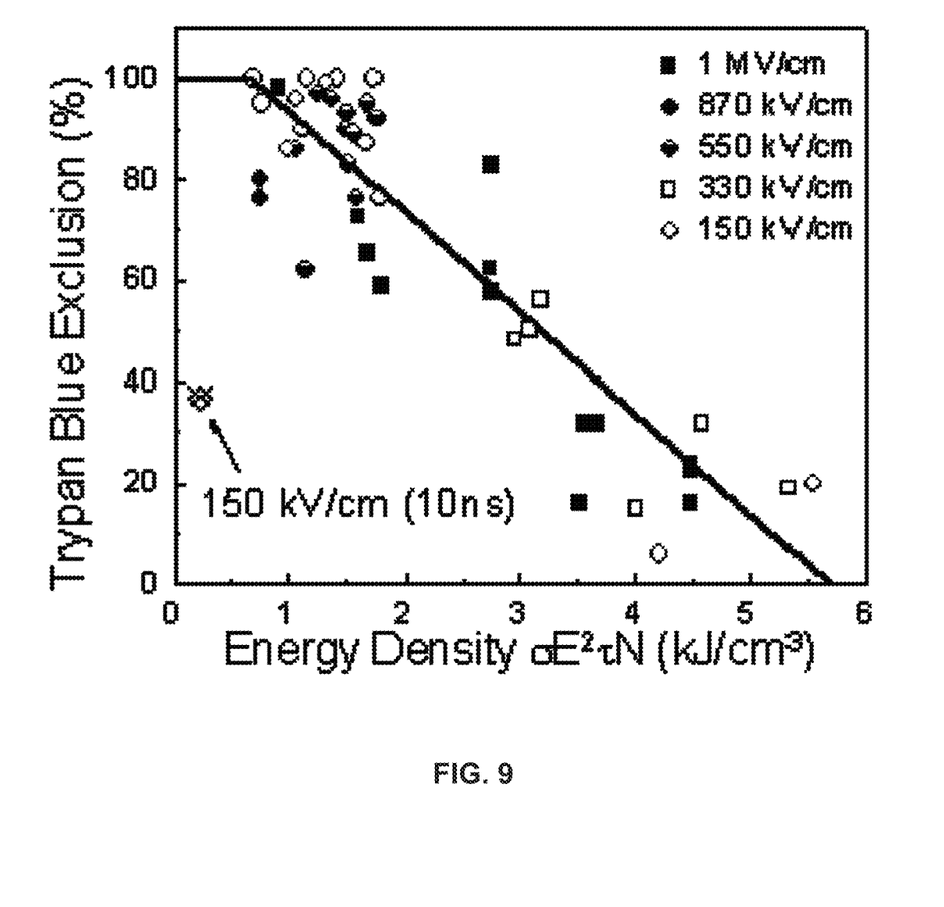
FIG. 9 is a graph depicting Trypan blue exclusion fraction versus electrical energy density. Variables were the electric field intensity which was varied between 150 kV/cm and 1 MV/cm, and the number of pulses which was varied between 1 and 20,000.

Whereas the effect of picoseconds electrical pulses on fibrils is substantial in the electrical parameter range of the studies, the lethal effect on healthy cells is less pronounced. Experiments with longer pulses (800 ps) have shown that it requires much higher electric fields (e.g., 550 kV/cm) to eliminate cells, in this case melanoma cells as shown in FIG. 8. More specifically, FIG. 8 is a graph depicting Trypan blue exclusion, 1 hour after pulsing, and caspase activity, measured 4.5 hours after pulsing, versus number of 800 ps pulses with average electric field amplitudes of 550 kV/cm (trypan blue exclusion) and 49-kV/cm (caspase activity), respectively. This can also be seen using the dose response graph shown in FIG. 9. More specifically, FIG. 9 is a graph depicting Trypan blue exclusion fraction versus electrical energy density. Variables were the electric field intensity which was varied between 150 kV/cm and 1 MV/cm, and the number of pulses which was varied between 1 and 20,000.

Assuming that shorter pulses (150 ps) as used in this method will always have a lesser effect on cell viability than longer pulses, and that the lethal effects of these pulses on neurons is comparable to that of melanoma cells, we can from this graph show that 4000, 40 kV/cm pulses as well as 1000, 100 kV/cm pulses should not affect the viability of the neurons or other healthy cells surrounding the amyloid fibrils.

It is to be understood that while the invention in has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

What is claimed is:

1. A method for treating a condition aggravated by the presence of amyloid fibrils, comprising:
  applying one or more ultra-short pulses to target tissue comprising amyloid fibrils, wherein each ultra-short pulse produces an electrical field in the target tissue, and wherein the one or more ultra-short pulses are sufficient to change a molecular structure of said amyloid fibrils.

2. The method according to claim 1, wherein the one or more ultra-short pulses are sufficient to change a molecular structure of said amyloid fibrils without destroying healthy cells surrounding said target tissue.

3. The method according to claim 1, wherein a duration of at least one of said one or more ultra-short pulses ranges from 1 ps to 1 µs.

4. The method according to claim 1, wherein an electrical field applied to said target tissue by said one or more ultra-short pulses ranges from 1 kV/cm to 1 MV/cm.

5. The method according to claim 1, wherein an amplitude of at least one of the one or more ultra-short pulses ranges from 100 V to 1 MV.

6. The method according to claim 1, wherein the target tissue comprises brain tissue, intra-articular tissue, or other bodily tissue.

7. The method according to claim 1, wherein said change in molecular structure comprises breaking hydrogen bonds.

8. The method according to claim 1, wherein said change in molecular structure comprises breaking hydrogen bonds and as well as other interactions.

9. The method according to claim 1, further comprising:
positioning an electrode device comprising a working electrode within a subject being treated such that each ultra-short pulse produces an electrical field in said target tissue ranging from 1 kV/cm to 1 MV/cm.

10. The method according to claim 9, wherein said electrode device comprises a wave guide, positioned within a catheter.

11. The method according to claim 1, further comprising:
positioning an antennae transmitting electromagnetic radiation as a result of receiving said one or more ultra-short pulses thereby producing an electrical field in said target tissue ranging from 1 kV/cm to 1 MV/cm.

12. The method according to claim 11, wherein said antennae is external to a subject being treated.

13. The method according to claim 1 further comprising identifying the target tissue comprising amyloid fibrils to which the one or more ultra-short pulses will be applied.

* * * * *